US008236536B2

(12) United States Patent
Varanasi et al.

(10) Patent No.: US 8,236,536 B2
(45) Date of Patent: Aug. 7, 2012

(54) SACCHARIFYING CELLULOSE

(75) Inventors: Sasidhar Varanasi, Toledo, OH (US); Constance Ann Schall, Sylvania, OH (US); Anantharam Prasad Dadi, Toledo, OH (US)

(73) Assignee: The University of Toledo, Toledo, OH (US)

( * ) Notice: Subject to any disclaimer, the term of this patent is extended or adjusted under 35 U.S.C. 154(b) by 328 days.

(21) Appl. No.: 12/687,049

(22) Filed: Jan. 13, 2010

(65) Prior Publication Data

US 2010/0233773 A1   Sep. 16, 2010

Related U.S. Application Data

(62) Division of application No. 11/710,357, filed on Feb. 23, 2007, now Pat. No. 7,674,608.

(51) Int. Cl.
   *C12P 7/10*      (2006.01)
   *C12P 19/14*     (2006.01)
   *C12P 19/20*     (2006.01)

(52) U.S. Cl. ............... 435/165; 435/96; 435/99

(58) Field of Classification Search ............ 435/96, 435/99, 165
   See application file for complete search history.

(56) References Cited

U.S. PATENT DOCUMENTS

| | | | |
|---|---|---|---|
| 1,943,176 | A | 1/1934 | Graenacher |
| 2,990,233 | A | 6/1961 | Pacsu et al. |
| 4,174,976 | A | 11/1979 | Tsao et al. |
| 4,260,685 | A | 4/1981 | Pilipski |
| 4,968,350 | A | 11/1990 | Bindschaedler et al. |
| 5,372,939 | A | 12/1994 | Lastick et al. |
| 5,916,780 | A | 6/1999 | Foody et al. |
| 6,808,557 | B2 | 10/2004 | Holbrey et al. |
| 6,824,599 | B2 | 11/2004 | Swatloski et al. |
| 7,049,485 | B2 | 5/2006 | Sticklen et al. |
| 7,674,608 | B2 | 3/2010 | Varanasi et al. |
| 2004/0053373 | A1 | 3/2004 | Foody et al. |
| 2005/0288484 | A1 | 12/2005 | Holbrey |
| 2007/0006774 | A1 | 1/2007 | Rogers |
| 2007/0199613 | A1 | 8/2007 | Bouldin et al. |
| 2007/0215300 | A1 | 9/2007 | Upfal et al. |
| 2007/0231918 | A1 | 10/2007 | Zeng |
| 2008/0023162 | A1 | 1/2008 | Myllymaki et al. |
| 2008/0164440 | A1 | 7/2008 | Maase et al. |
| 2008/0185112 | A1 | 8/2008 | Argyropoulos |
| 2008/0188636 | A1 | 8/2008 | Argyropoulos et al. |
| 2008/0190013 | A1 | 8/2008 | Argyropoulos ............ 44/307 |
| 2008/0190321 | A1 | 8/2008 | Maase et al. |
| 2008/0213850 | A1 | 9/2008 | Shimoda et al. |
| 2008/0227162 | A1 | 9/2008 | Varanasi et al. |
| 2008/0269477 | A1 | 10/2008 | Stegmann |
| 2009/0020112 | A1 | 1/2009 | Massonne |
| 2009/0044942 | A1 | 2/2009 | Gupta |
| 2009/0062524 | A1 | 3/2009 | Massonne et al. |
| 2009/0088564 | A1 | 4/2009 | Luo et al. |
| 2009/0093027 | A1 | 4/2009 | Balan et al. |
| 2009/0143597 | A1 | 6/2009 | Dyson et al. |
| 2009/0176286 | A1 | 7/2009 | O'Connor et al. |
| 2009/0198046 | A1 | 8/2009 | Fanselow et al. |
| 2009/0203899 | A1 | 8/2009 | Buchanan et al. |
| 2009/0229599 | A1 | 9/2009 | Zhang |
| 2009/0234146 | A1 | 9/2009 | Cooney et al. |
| 2009/0270248 | A1 | 10/2009 | Earl et al. |
| 2009/0326286 | A1 | 12/2009 | Yie et al. |
| 2010/0055237 | A1 | 3/2010 | Zorn et al. |
| 2010/0151111 | A1 | 6/2010 | Nielsen et al. |

FOREIGN PATENT DOCUMENTS

| | | |
|---|---|---|
| WO | WO 2005/017252 | 2/2005 |
| WO | WO 2005/090563 | 9/2005 |
| WO | WO 2007/111605 | 10/2007 |
| WO | WO 2008/043837 | 4/2008 |
| WO | WO 2008/090155 | 7/2008 |
| WO | WO 2008/090156 | 7/2008 |
| WO | WO 2008/095252 | 8/2008 |
| WO | WO 2009/018469 | 2/2009 |
| WO | WO 2009/024607 | 2/2009 |
| WO | WO 2009/030949 | 3/2009 |
| WO | WO 2009/030950 | 3/2009 |
| WO | WO 2009/105236 | 8/2009 |
| WO | WO 2009/124240 | 10/2009 |

OTHER PUBLICATIONS

Dadi et al., "Enhancement of Cellulose Saccharification Kineics Using an Ionic Liquid Pretreatment Step", Wiley InterScience, Biotechnology and Bioengineering, vol. 95, No. 5 (2006).

Ghose, "Measurement of Cellulase Activities", International Union of Pure and Applied Chemistry, vol. 59, No. 2, pp. 257-268 (1987).

Kilpelainen et al., "Dissolution of Wood in Ionic Liquids", Journal of Agricultural and Food Chemistry, vol. 55, pp. 9142-9148 (2007.

(Continued)

*Primary Examiner* — Herbert J Lilling

(74) *Attorney, Agent, or Firm* — Hunton & Williams LLP

(57) ABSTRACT

Dissolution, partial dissolution or softening of cellulose in an ionic liquid (IL) and its subsequent contact with anti-solvent produces regenerated cellulose more amorphous in structure than native cellulose, which can be separated from the IL/anti-solvent mixture by mechanical means such as simple filtration or centrifugation. This altered morphology of IL-treated cellulose allows a greater number of sites for enzyme adsorption with a subsequent enhancement of its saccharification. The IL-treated cellulose exhibits significantly improved hydrolysis kinetics with optically transparent solutions formed after about two hours of reaction. This provides an opportunity for separation of products from the catalyst (enzyme) easing enzyme recovery. With an appropriate selection of enzymes, initial hydrolysis rates for IL-treated cellulose were up to two orders of magnitude greater than those of untreated cellulose. Due to the non-volatility of the IL, anti-solvent can be easily stripped from the IL/anti-solvent mixture for recovery and recycle of both the ionic liquid and anti-solvent.

28 Claims, 6 Drawing Sheets

OTHER PUBLICATIONS

Miller, "Use of Dinitrosalicylic Acid Reagent for Determination of Reducing Sugar", Analytical Chemistry, vol. 31, No. 3, Mar. 1959.

Segal et al., "An Empirical Method for Estimating the Degree of Crystallinity of Native Cellulose Using the X-Ray Diffractometer", Textile Research Journal, pp. 786-794 (1959).

Swatloski et al., "Dissolution of Cellose with Ionic Liquids", Journal of American Chemical Society, vol. 124, pp. 4974-4975 (2002).

Zhang et al., 1-Allyl-3-methylimidazolium Chloride Room Temperature Ionic Liquid: A New and Powerful Nonderivatizing Solvent for Cellulose, American Chemical Society, Macromolecules, vol. 38, pp. 8272-8277 (2005).

Non-Final Office Action mailed Oct. 29, 2009 in co-pending U.S. Appl. No. 12/075,762.

Co-Pending U.S. Appl. No. 12/687,049, filed Jan. 13, 2010, entitled "Saccharifying Cellulose".

Dadi, "Mitigation of Cellulose Recalcitrance to Enzymatic Hydrolysis by Ionic Liquid Pretreatment", Applied Biochemistry and biotechnology, vol. 136-140, Humana Press, Inc. (2007).

Eggeman et al., "Process and Economic Analysis of Pretreatment Technologies", Bioresource Technology, vol. 96, pp. 2019-2025 (2005).

Fort, "Can Ionic Liquids Dissolve Wood? Processing and Analysis of Lignocellulosic Materials with 1-n-butyl-3-methylimidazolium chloride", The Royal Society of Chemistry, Green Chemistry, vol. 9, pp. 63-69 (2007).

International Search Report mailed Oct. 3, 2008 for International Patent Application No. PCT/US2008/03357.

Kilpelainen et al., "Dissolution of Wood in Ionic Liquids", Journal of Agricultural and Food Chemistry, vol. 55, pp. 9142-9148 (2007).

Kim and Holzapple, "Lime Pretreatment and Enzymatic Hydrolysis of Corn Stover", Bioresource Technology, vol. 96, pp. 1994-2006 (2005).

Kim, "Pretreatment and Fractionation of Corn Stover by Ammonia Recycle Percolation Process", Bioresource Technology, vol. 96, pp. 2007-2013 (2005).

Lloyd and Wyman, Combined Sugar Yields for Dilute Sulfuric Acid Pretreatment Pretreatment of Corn Stover Followed by Enzymatic Hydrolysis of the Remaining Solids, Bioresource Technology, 96, pp. 1967-1977 (2005).

Mosier et al., Optimization of pH Controlled Liquid Hot Water Pretreatment of Corn Stover, Bioresource Technology, 96, pp. 1986-1993 (2005).

Non-Final Office Action mailed May 8, 2009 in U.S. Appl. No. 11/710,357, now U.S. Patent No. 7,674,608.

Teymouri et al., "Optimization of the Ammonia Fiber Explosion (AFEX) Treatment Parameters for Enzymatic Hydrolysis of Corn Stover", Bioresource Technology, vol. 96, pp. 2014-2018 (2005).

Wyman et al., "Coordinated Development of Leading Biomass Pretreatment Technologies", Bioresource Technology, 96, pp. 1959-1966 (2005).

Wyman, Comparative Sugar Recovery Data from Laboratory Scale Application of Leading Pretreatment Technologies to Corn Stover, Bioresource Technology, 96, pp. 2026-2032 (2005).

Zhang et al, "Fractioning Recalcitrant Lignocellulose at modest Reaction Conditions", Biotechnology and Bioengineering, vol. 97, No. 2, pp. 214-223, Jun. 2007.

Zhang et al., "1-Allyl-3-methylimidazolium Chloride Room Temperature Ionic Liquid: A New and Powerful Nonderivatizing Solvent for Cellulose", American Chemical Society, Macromolecules, vol. 38, pp. 8272-8277 (2005).

Zhang, "A Transition from Cellulose Swelling to Cellulose Dissolution by o-Phosphoric Acid: Evidence from Enzymatic Hydrolysis and Supramolecular Structure", Biomacromolecules, vol. 7, pp. 644-648 (2006).

Non-Final Office Action mailed Jun. 24, 2010 in U.S. Appl. No. 12/075,762.

Non-Final Office Action mailed Oct. 29, 2009 in U.S. Appl. No. 12/075,762.

SACCHARIFYING CELLULOSE

REFERENCE TO RELATED APPLICATIONS

This application is a Divisional application of U.S. patent application Ser. No. 11/710,357, filed Feb. 23, 2007, the disclosure of which is herein incorporated by reference in its entirety.

TECHNICAL FIELD

This invention relates to saccharifying cellulose from biomass. Cellulose is the most abundant renewable resource in the world. It is a major fraction of plant biomass, which is the feedstock, for "future biorefineries" with the potential to replace the conventional petrochemical refineries in an economy based on renewable resources.

BACKGROUND OF THE INVENTION

The utilization of lignocellulosic waste materials, such as cornstalks, sawdusts, straws, bagasse, and the like, has been the subject of strong interest recently, particularly with respect to utilization of such agricultural and waste materials for developing alternate sources of fuels, chemicals, glucose and the like. Lignocellulose is commonly referred to as biomass.

Lignocellulosic materials include three principal components—cellulose (30-40%), hemicellulose (20-30%), and lignin (5-30%). In its natural state, cellulose is highly crystalline in structure with individual cellulose polymer chains held together by strong hydrogen bonding and van der Waals forces. The individual cellulose chains are linear condensation polymer molecules made up of anhydroglucose units joined together by β-1,4 glycosidic bonds with degrees of polymerization (DP) ranging, typically, from 1,000 to 15,000 units. The high crystallinity of cellulose, while imparting structural integrity and mechanical strength to the material, renders it recalcitrant towards hydrolysis aimed at producing glucose—the feedstock for producing fuels and chemicals—from this polysaccharide. In general, neither the water molecules nor the catalysts for hydrolysis (saccharification) are able to easily penetrate the crystalline matrix.

Cellulose hydrolysis to glucose is most often catalyzed using mineral acids or enzymes (cellulases). Cellulase hydrolysis is preferred over mineral acid hydrolysis for several reasons: acid hydrolysis leads to formation of undesirable degradation products of glucose that significantly lower glucose yield and inhibit subsequent fermentation; requires expensive corrosion-resistant materials; and poses disposal problems. Glucose degradation products observed with acid pretreatment or hydrolysis include hydroxymethyl furfural (HMF) and furfural which inhibit downstream fermentation to ethanol.

On the other hand, cellulase enzymes are very specific in their action, producing virtually no glucose degradation products. Cellulases (of fungal or bacterial origin) are in fact a mixture of enzymes which act in concert and synergistically. Special materials of construction are not required with cellulase-catalyzed hydrolysis. However, cellulose hydrolysis in aqueous media suffers from slow reaction rates because the substrate (cellulose) is a water-insoluble crystalline biopolymer. Therefore, the enzymes have to accomplish the hydrolytic decomposition via first adsorbing on the cellulose surface, partially stripping the individual polymer chains from the crystal structure, and then cleaving the glycoside bonds in the chain. Adsorption sites of crystalline cellulose are very limited due to the tight packing arrangement of cellulose fibrils which not only excludes the enzymes but also largely excludes water.

Cellulose is very difficult to dissolve due to the extensive network of inter and intra-molecular bonds and interactions between cellulose fibrils. Ionic liquids have recently been shown to be novel solvents for dissolution of cellulose capable of dissolving large amounts of cellulose at mild conditions (Swatloski, R. P. et al., J. Am. Chem. Soc., 2002, 124, 4974-4975; Zhang, H. et al., Macromolecules, 2005, 38, 8272-8277). Ionic liquids (ILs) are salts that typically melt below ~100° C. With their low volatility, fluidity at ambient temperatures, and unique solvent properties, ILs comprise a class of prospective solvents that are potentially 'green' due to their minimal air emissions. Our invention exploits these properties of ionic liquids to enhance the saccharification of cellulose.

SUMMARY OF THE INVENTION

We have now invented an efficient route for saccharifying cellulose from biomass for fuel and chemical production.

Hydrolysis of cellulose to glucose is critically important in producing fuels and chemicals from renewable feedstocks. Cellulose hydrolysis in aqueous media suffers from slow reaction rates because cellulose is a water-insoluble crystalline biopolymer. To accomplish its hydrolysis, the hydrolyzing enzymes (cellulases) and water must penetrate the crystalline fibrils. Pretreatment methods which increase the surface area accessible to water and cellulases are vital to improving the hydrolysis kinetics and conversion of cellulose to glucose. In a novel technique, the cellulose is dissolved or partially dissolved in an ionic liquid (IL) and subsequently recovered as an amorphous precipitate or a solid of lower crystallinity index by rapidly quenching the solution with an anti-solvent. Hydrolysis kinetics of the recovered cellulose are significantly enhanced. Because of their extremely low volatility, ionic liquids are expected to have minimal environmental impact. With an appropriate selection of enzymes, initial hydrolysis rates for recovered cellulose were up to ninety times greater than those of untreated cellulose.

DETAILED DESCRIPTION OF THE INVENTION

Figure 1:
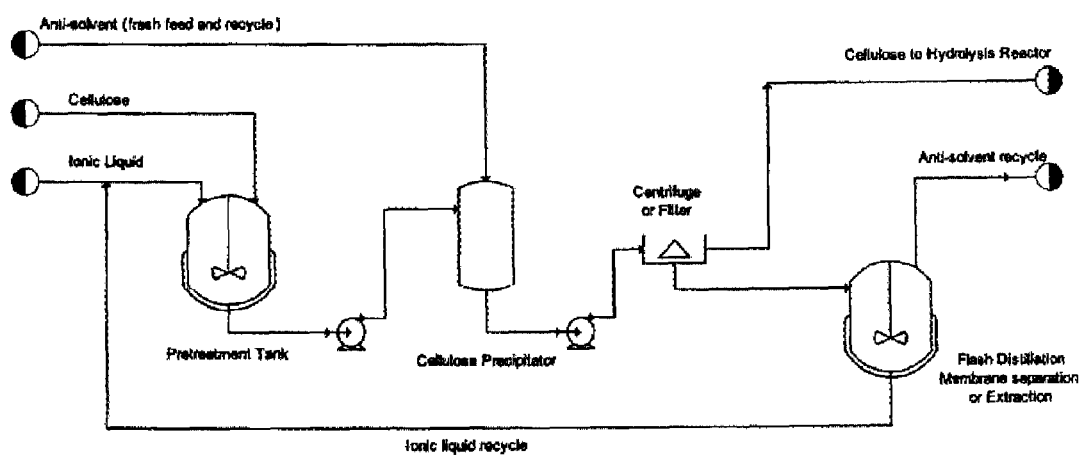
FIG. 1: is a schematic diagram of a unit for the regeneration of cellulose with ionic liquids.

The goal of this pretreatment invention is to open the structure of cellulose to make it accessible to water and the component enzymes of cellulases in order to increase the rate of hydrolysis of cellulose to glucose or soluble glucose oligomers. In our approach, ionic liquids are used to dissolve or partially dissolve crystalline cellulose. Any ionic liquid that is capable of dissolving cellulose can be used in the pretreatment strategy outlined here. The disclosure of U.S. Pat. No. 6,824,599 herein is incorporated by reference. The cellulose dissolution step is followed by rapid quenching with an "anti-solvent" such as water, acetonitrile or alcohol, the high affinity of which towards the IL forces the latter to reject all the dissolved cellulose via a preferential solute-displacement mechanism. The resulting cellulose is either an amorphous precipitate or a solid of significantly lower crystallinity depending on whether the initial cellulose weight percent is lower or higher than its solubility limit in the IL. The rejected cellulose can be separated from the IL-anti-solvent solution through mechanical separations such as centrifugation or filtration. The ionic liquids are nonvolatile and they can be recovered from the anti-solvent/IL mixture by flash distillation, solvent extraction, membranes or ion exchange techniques (FIG. 1).

The recovered cellulose is referred to as regenerated cellulose (RC) when it is an amorphous precipitate, as is the case when the cellulose completely dissolves in the IL during incubation. However, when the initial cellulose weight percent is more than its solubility limit in the IL, only partial dissolution of cellulose occurs during incubation. Subsequent anti-solvent treatment provides a cellulose mix of RC and IL-swollen partially crystalline cellulose (PCC). In what follows, cellulose samples recovered following anti-solvent treatment are referred to as "IL-treated cellulose" irrespective of whether the resulting cellulose is RC or a mixture of RC and PCC. In solvent-swollen cellulose the degree of crystallinity of cellulose is progressively reduced as the extent of swelling increases but is not eliminated, whereas regenerated-cellulose is essentially amorphous. The hydrolysis rates of cellulose depend on the extent of swelling with the maximal improvement in hydrolysis with amorphous regenerated-cellulose.

The amount of cellulose that can be completely dissolved in the IL during incubation was shown to vary depending on whether the mixture was subjected to conventional heating with agitation or microwave irradiation with intermittent agitation. The latter procedure was shown to be capable of bringing larger amounts of cellulose to complete dissolution compared to conventional heating (Swatloski, R. P. et al., J. Am. Chem. Soc., 2002, 124, 4974-4975). Regardless of which approach is taken for dissolving cellulose, quenching the solution with an anti-solvent for cellulose renders the precipitate essentially amorphous, providing significant improvement in hydrolysis. Thus, the proposed invention of using IL-pretreatment to obtain readily hydrolysable cellulose can be benefited by all means capable of dissolving large amount of cellulose in the IL.

Example 1

Structure of Regenerated Cellulose (RC)

X-ray powder diffraction (XRD) data were obtained for IL-treated cellulose to assess crystallinity of recovered samples. Cellulose was fully dissolved in BMIMCl before precipitation with addition of anti-solvent for experiments outlined in this example. Anti-solvent selection, incubation time and temperature were varied.

Micro-crystalline cellulose, Avicel PH-101 (FMC Corp., Philadelphia, Pa.) was obtained from Sigma Aldrich, St. Louis, Mo. A 5% (w/w) cellulose solution was prepared by combining 50 mg of cellulose with 950 mg of 1-n-butyl-3-methylimidazolium chloride BMIMCl in a 5 ml autoclave vial. The vial and the contents were heated in a block heater to 130° C. and incubated for 10 minutes. The samples were gently stirred by placing the block heater on an orbital shaker.

Water, methanol and ethanol were used as anti-solvents for precipitating cellulose from BMIMCl. About 2 ml of anti-solvent was added to the cellulose/BMIMCl mixture. A precipitate immediately formed. The sample was briefly centrifuged and supernatant was removed. The sample was washed five to six times with additions of anti-solvent, centrifuged and supernatant removed. Smooth films for X-ray powder diffraction (XRD) data collection were cast at room temperature with RC and untreated cellulose on microscope slides. XRD data for these films were generated at 25° C. with an XPERT' PRO powder diffractometer with an Xcelerator' detector (PANalytical, ALMELO, The Netherlands) using Nickel filtered CuKα radiation. Samples were scanned over the angular range 6.0-45.0°, 2θ, with a step size of 0.05°, and step time of 10 seconds.

Figure 2:
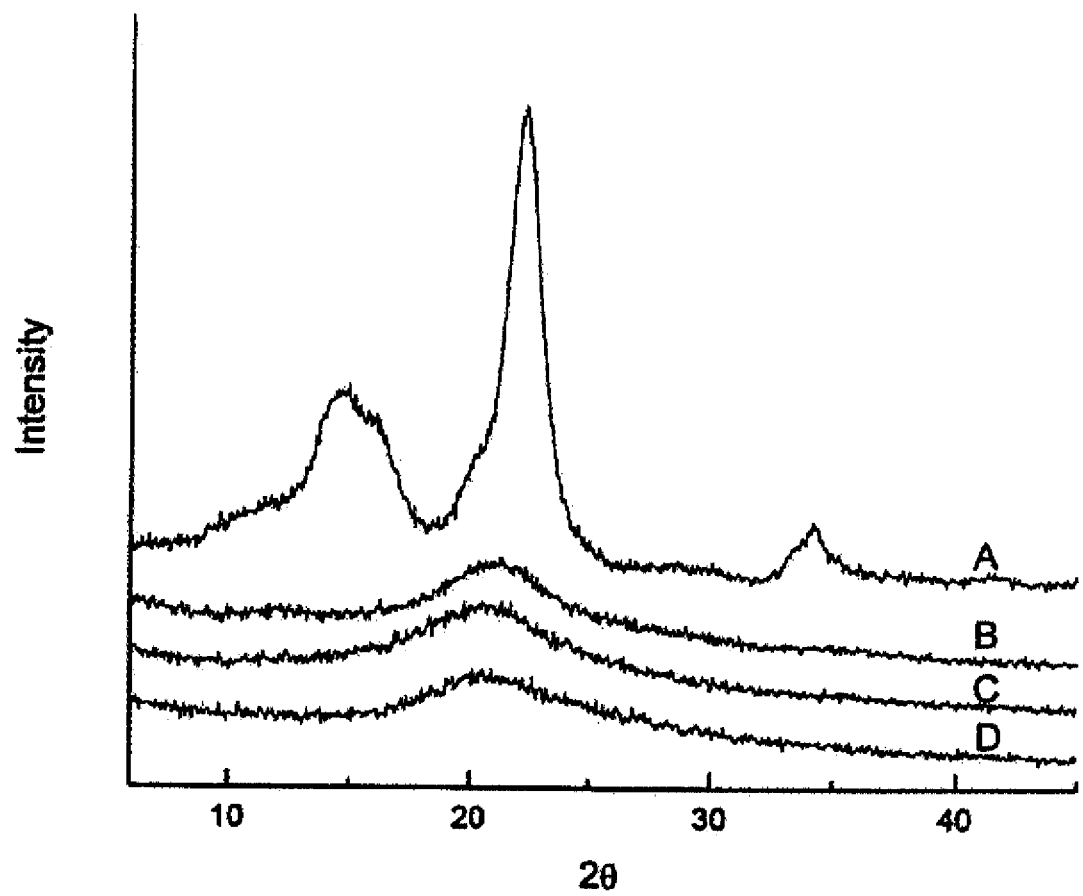
FIG. 2: shows X-ray powder diffraction patterns of untreated and regenerated Avicel. Untreated Avicel, (A), exhibited a significantly greater degree of crystallinity than that of regenerated samples (B) through (D). Regenerated samples were incubated in BMIMCl at 130° C. for two hours and precipitated with (B) deionized water, (C) methanol, or (D) ethanol.

As seen in FIG. 2 cellulose regenerated with all the selected anti-solvents produced amorphous cellulose whereas the untreated cellulose is highly crystalline. In additional XRD experiments, incubation time and temperature were varied from 10 to 180 minutes and from 130 to 150° C. with complete dissolution of cellulose (Dadi, A. P., S. Varanasi, C. A. Schall (2006) Biotechnology and Bioengineering, 95 (5), 904-910). The resulting regenerated cellulose structure was amorphous. XRD results suggest that during pretreatment with IL and anti-solvent cellulose crystallinity is disrupted. Rapid precipitation with anti-solvent may prevent the restructuring of the dissolved cellulose into its crystalline form.

Example 2

Initial Hydrolysis Rates of Regenerated Cellulose by Cellulase

For hydrolysis experiments, Avicel was regenerated by dissolution in BMIMCl followed by precipitation with water, methanol, or ethanol. Alternative anti-solvents methanol and ethanol were examined because BMIMCl is more easily recovered, following cellulose regeneration, from volatile organic solvents than water through a simple distillation step. Batch enzymatic hydrolysis of regenerated and untreated cellulose was carried out at 50° C. in a reciprocating shaker bath. Total batch volume was approximately 3 ml with a cellulase enzyme concentration of 60 FPU/g glucan, and substrate concentration of about 17 mg/ml. Solutions were buffered with 0.05M sodium citrate, pH 4.8. The enzyme reaction was monitored by withdrawing samples from the supernatant periodically and measuring release of soluble reducing sugars by the DNS assay (Miller G L. (1959) Anal. Chem. 31 (3): 426-428). Untreated and regenerated cellulose were hydrolyzed using the same cellulase (from *T. reesei*) stock solution. The untreated cellulose controls were run concurrently with all regenerated cellulose hydrolysis experiments to eliminate potential differences in temperature history or enzyme loading.

The resulting initial rates of hydrolysis of regenerated and untreated cellulose to soluble reducing sugars as measured by total soluble reducing sugars are shown in Table 1. Initial rates of enzymatic hydrolysis of regenerated cellulose were at least fifty times that of untreated cellulose. All anti-solvents studied appear to lead to similar enhancement in initial saccharification rates (Table 1).

TABLE 1

Initial rate of formation of total soluble reducing sugars measured by DNS assay in enzymatic hydrolysis of Avicel cellulose.

| Anti-solvent | Initial rate of formation of soluble reducing sugars (mg ml$^{-1}$min$^{-1}$) | Rate Enhancement* |
|---|---|---|
| water | 0.6473 | 52 |
| methanol | 0.6823 | 55 |
| ethanol | 0.6473 | 53 |
| untreated | 0.0125 | — |

17 mg/ml of regenerated or untreated Avicel samples were hydrolyzed using a cellulase activity of 60 FPU/g glucan. Regenerated cellulose samples were incubated in BMIMCl for 10 minutes at 130° C. and precipitated using the anti solvents water, methanol, or ethanol. Rates are calculated from data obtained in the first 20 minutes of hydrolysis. (Dadi, A. P., S. Varanasi, C. A. Schall (2006) Biotechnology and Bioengineering, 95(5), 904-910)
*Rate enhancement is defined as the ratio of initial rate of reducing sugars released for regenerated cellulose divided by that of untreated cellulose.

Example 3

Initial Hydrolysis Rates of Regenerated Cellulose by Cellulases in the Presence of Additional β-Glucosidase In this example the effect of augmenting cellulase (Celluclast 1.5 L, a *Trichoderma reesei* cellulase) with additional β-glucosidase (Novozyme 188, a cellobiase) on the rates of hydrolysis of untreated and regenerated cellulose was investigated. The enzymes were obtained from Novozyme Corp., Bagsvaerd, Denmark. Cellulase activity was determined by the standard filter paper assay and expressed as filter paper units (FPU) per gram of glucan (Gosh, T. K., (1987), *Pure Appl. Chem.*, 59, 257-268). Cellobiase activity was determined by a cellobiose hydrolysis assay (Gosh, T. K., (1987), *Pure Appl. Chem.*, 59, 257-268) and expressed as cellobiose units (CBU) per gram of glucan.

A batch volume of 3 ml with a cellulose concentration of 16.7 mg/ml was used with both untreated cellulose and regenerated-cellulose (recovered from 5% (w/w) cellulose-BMIMCl mixture using de-ionized water as anti-solvent). The enzyme loadings were varied from 8 to 32 FPU/g glucan of Celluclast 1.5 L and 0 to 83 CBU/g glucan of Novozyme 188. The enzyme reaction was monitored by withdrawing 20 µl samples from the supernatant periodically. Withdrawn samples were diluted 10 times and heated to 100° C. for 5 minutes. Untreated and IL-treated cellulose were hydrolyzed using the same cellulase and β-glucosidase stock solutions. The untreated-cellulose controls were run concurrently with all the IL-treated-cellulose hydrolysis experiments to eliminate potential differences in temperature history or enzyme loading.

The released reducing sugars were measured by the dinitrosalicylic acid (DNS) method using D-glucose as a standard. Released glucose was determined separately by high performance liquid chromatography (HPLC) using a HPX-87 P column (Bio-Rad Laboratories Inc., Hercules, Calif.) at 80° C. equipped with a refractive index detector. The mobile phase was deionized water with a flow rate of 0.6 ml/minute.

The initial rate of soluble reducing sugar formation of untreated cellulose and cellulose regenerated from a 5% cellulose/BMIMCl mixture is shown in Table 2 for various enzyme loadings, with and without β-glucosidase addition.

TABLE 2

Effect of additional β-glucosidase on hydrolysis. Initial rate of formation of total reducing sugars, measured by DNS assay.

| Enzyme activity per g of glucan | | Initial rate (mg ml$^{-1}$min$^{-1}$) | | |
|---|---|---|---|---|
| Cellulase (FPU) | β-glucosidase (CBU) | Untreated Cellulose | Regenerated Cellulose | Rate Enhancement* |
| 8 | 0 | 0.0004 | 0.0047 | 12 |
| 8 | 83 | 0.0004 | 0.0320 | 71 |
| 16 | 0 | 0.0043 | 0.0427 | 10 |
| 16 | 83 | 0.0044 | 0.3915 | 89 |
| 32 | 0 | 0.0110 | 0.3953 | 36 |
| 32 | 83 | 0.0140 | 0.5030 | 36 |

Rates are calculated from analysis of supernatant sampled during the first 20 minutes of hydrolysis. Regenerated cellulose was formed by incubating samples of 5% cellulose in ionic liquids (BMIMCI) at 130° C. for 10 minutes followed by precipitation with water.
*Rate enhancement is defined as the ratio of initial rate of reducing sugars released for regenerated cellulose divided by that of untreated cellulose.

The rate enhancement, defined as the ratio of initial hydrolysis rate of IL-treated cellulose to that of untreated cellulose, appears highest for an enzyme loading of 16 FPU/g glucan with addition of β-glucosidase at 83 CBU/g glucan. At these enzyme loadings the hydrolysis rate of regenerated cellulose is nearly two orders of magnitude greater than that of untreated cellulose. For modest cellulase activities (8 and 16 FPU/g glucan), the hydrolysis rates of regenerated cellulose increased significantly with addition of β-glucosidase (by 6 to 9 fold). This increase was not seen in untreated cellulose samples at similar cellulase activities (Table 2).

Example 4

Effect of the Residual Crystallinity of IL-Treated Cellulose on Hydrolysis

In this example, Avicel and BMIMCl or 1-allyl-3-methyl imidazolium chloride (AMIMCl) mixtures containing 5%, 10%, 15% and 30% (w/w) cellulose were incubated in a 5 ml autoclave vial. The vial and the contents were heated in a block heater to 120 to 130° C. for 10 to 30 minutes. The samples were gently stirred by placing the block heater on an orbital shaker.

Deionized water was used as an anti-solvent for recovering cellulose from the ionic liquids, BMIMCl and AMIMCl. About 2 ml of anti-solvent was added to the cellulose/ionic liquid mixture. A precipitate immediately formed. The sample was briefly centrifuged and supernatant was removed. The precipitated sample was washed with additional aliquots of water followed by the cellulose hydrolysis buffer solution.

During the incubation of Avicel in ionic liquids at 120° C. and 130° C., complete dissolution was observed for 5% (w/w) Avicel solutions in BMIMCl and AMIMCl. 10% solutions were completely dissolved in BMIMCl and almost completely dissolved in AMIMCl. For 15 and 30% (w/w) Avicel in ILs, only partial dissolution occurred. The maximum solubility of Avicel observed visually at 120° C. was 9% in AMIMCl and 13% in BMIMCl.

Samples of cellulose recovered following anti-solvent treatment of IL-cellulose mixtures and untreated-cellulose were examined by XRD. Crystallinity index, CrI, was determined from X-ray powder diffraction data (Segal, L., Creely, J. J., Martin, A. E., and Conrad, C. M. (1959) *Text. Res. J.* 29) and calculated using the formula: $CrI=[(I_{020}-I_{am})/I_{020}]\times 100$ where $I_{020}$ is the intensity above baseline at the 020 peak maximum near $2\theta$ 22.5° and $I_{am}$ is the minimum in peak intensity near $2\theta$ of 18°. A reduction in CrI was observed for all samples incubated in the ILs (Table 3). For cellulose concentrations below the solubility limit in the IL (5 and 10% (w/w)), the cellulose recovered following anti-solvent addition is essentially amorphous. Accordingly, the reduction in the measured CrI was greatest for 5 and 10% (w/w) samples and remains essentially the same for both ILs. However, with samples containing initial cellulose weight percent above its solubility limit in the IL (15 and 30% (w/w)), only partial dissolution of cellulose occurs during incubation. Subsequent anti-solvent treatment provides a cellulose mix of regenerated cellulose (RC) and partially crystalline cellulose (PCC). The proportion of PCC is expected to rise as the initial wt % of cellulose incubated in IL is increased. This gradual increase in PCC will lead to a corresponding increase in CrI as was observed from the CrI obtained from XRD measurement (Table 3).

TABLE 3

Effect of CrI of IL-treated Avicel on hydrolysis. Initial rate of formation of total soluble reducing sugars, measured by DNS assay during the enzymatic hydrolysis of Approx 17 mg/ml Avicel (with a cellulase activity of 16 FPU/g glucan and added β-glucosidase activity of 83 CBU/g glucan).

| Concentration of Avicel in IL | Initial rate (mg ml$^{-1}$min$^{-1}$) | Rate Enhancement* | Crystallinity Index (CrI) |
|---|---|---|---|
| Untreated | 0.0046 | — | 76.4 |
| 5% in AMIMCl | 0.3274 | 71 | 12.9 |
| 10% in AMIMCl | 0.3397 | 74 | 11.7 |
| 15% AMIMCl | 0.2304 | 50 | 15 |
| 30% AMIMCl | 0.1263 | 27 | 47.0 |
| 5% in BMIMCl | 0.3412 | 74 | 11.5 |
| 10% BMIMCl | 0.3763 | 82 | 11.6 |
| 15% BMIMCl | 0.289 | 63 | 14.2 |
| 30% BMIMCl | 0.2140 | 46 | 43.4 |

Rates are calculated from analysis of supernatant sampled during the first 20 minutes of hydrolysis. RC or a mixture of RC & PCC was formed by incubating cellulose in ionic liquids (AMIMCl/BMIMCl) at 120° C. for 30 minutes followed by contact with water. A mixture of RC & PCC formed at Avicel concentrations in IL above 10% (w/w).
*Rate enhancement is defined as the ratio of initial rate of reducing sugars released for regenerated cellulose divided by that of untreated cellulose.

The effect of crystallinity of recovered cellulose on hydrolysis was also investigated in this example. Batch volumes were adjusted for IL-treated cellulose samples to achieve the same cellulose concentration of 16.7 mg/ml employed with untreated cellulose. The resulting volumes were 3 ml, 6 ml, 9 ml and 18 ml, respectively, for cellulose samples recovered from IL-cellulose mixtures of 5%, 10%, 15% and 30% (w/w) cellulose. A constant enzyme loading of 16 FPU/g glucan with addition of β-glucosidase at 83 CBU/g glucan was used in all experiments conducted with various IL-treated-cellulose samples (incubation of 5, 10, 15 and 30% cellulose in the ionic liquids). The initial rates of hydrolysis for untreated and IL-treated-cellulose are shown in Table 3. The concentrations of total soluble sugars and glucose are shown as functions of time in FIGS. 3 and 4.

Initial rates of enzymatic hydrolysis of completely dissolved and regenerated cellulose samples (5 and 10%) were higher than the IL-treated-cellulose samples that were partially dissolved (15 and 30%) as seen in Table 3. Samples containing initial cellulose concentrations below 10% are within the solubility limit in IL, and above 10% are above the solubility limit in IL. Addition of anti-solvent to IL-cellulose mixtures produced regenerated-cellulose (RC) when the cellulose concentration is within the solubility limit and produced a mixture of RC and partially crystalline cellulose (PCC) above the solubility limit. Mixtures of RC and PCC have residual crystallinity (Table 3) which accounted for lower initial rates compared to RC samples.

Figure 3A:
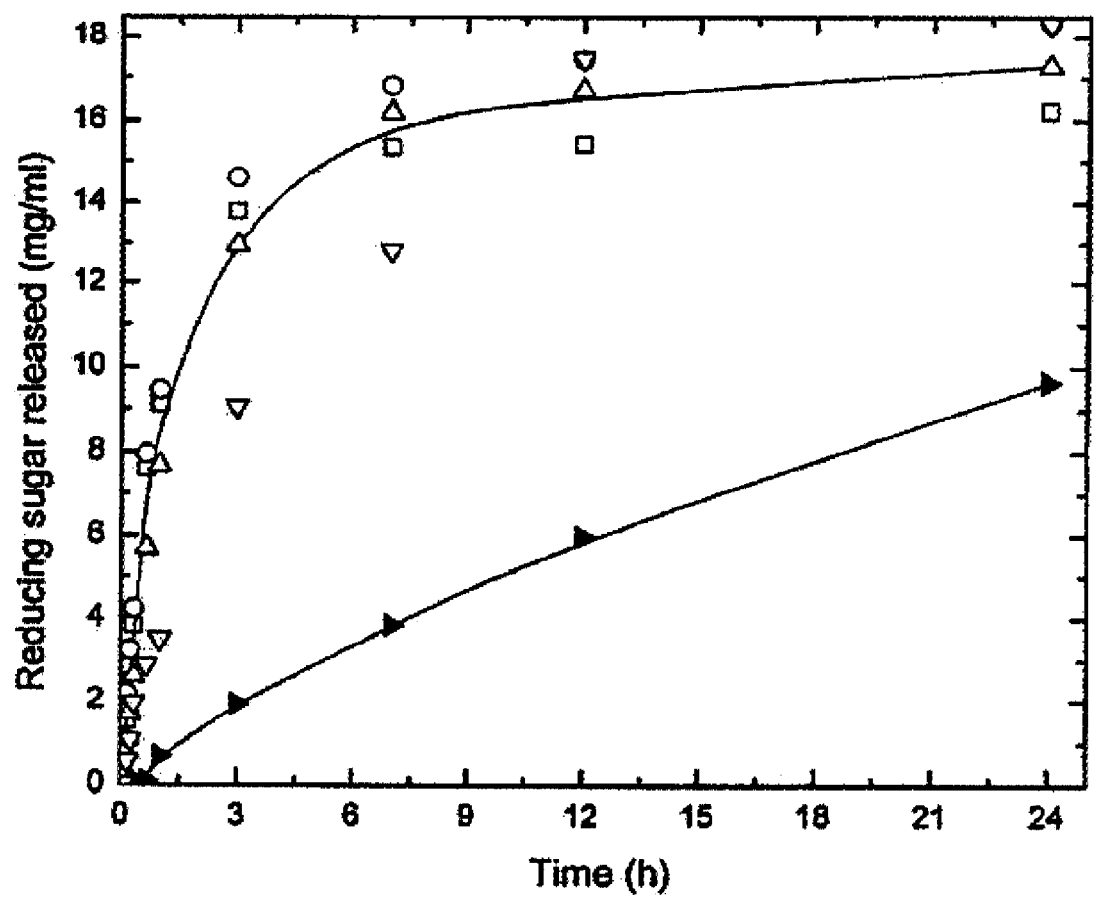
FIG. 3A: shows hydrolysis rates of IL incubated samples compared to those of untreated Avicel (▸), 5% (□), 10% (○), 15% (Δ), 30% (∇) Avicel samples were incubated for 30 minutes in AMIMCl at 120° C., and precipitated with deionized water. Conversion of cellulose to sugars for batch samples of ~17 mg/ml Avicel hydrolyzed with *T. reesei* cellulase activity of 16 FPU/g glucan and supplemental cellobiase activity of 83 CBU/g glucan at 50° C. is shown as a function of time for total soluble sugars (measured using a DNS assay).
Figure 3B:
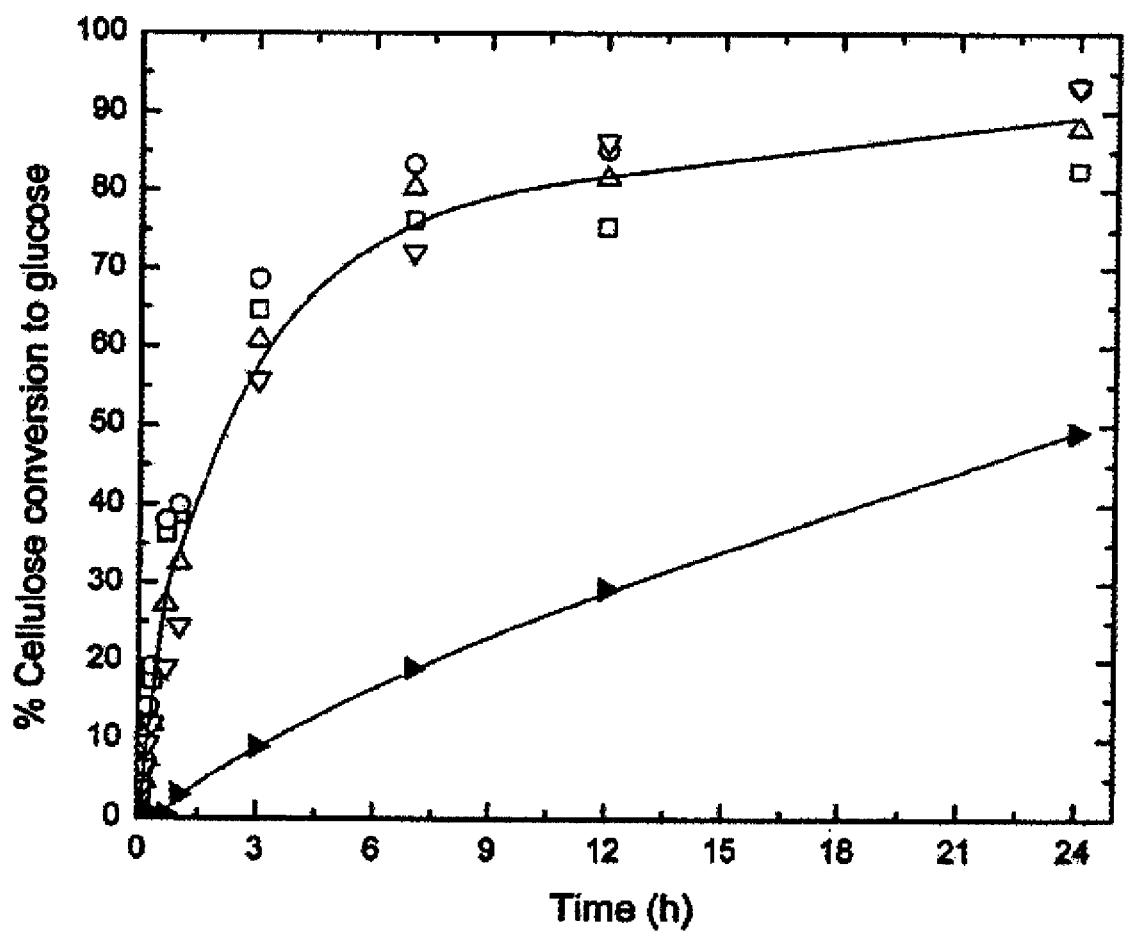
FIG. 3B: shows hydrolysis rates of IL incubated samples compared to those of untreated Avicel (▸), 5% (□), 10% (○), 15% (Δ), 30% (∇) Avicel samples were incubated for 30 minutes in AMIMCl at 120° C., and precipitated with deionized water. Conversion of cellulose to sugars for batch samples of ~17 mg/ml Avicel hydrolyzed with *T. reesei* cellulase activity of 16 FPU/g glucan and supplemental cellobiase activity of 83 CBU/g glucan at 50° C. is shown as % cullulose conversion to glucose (measured by HPLC).
Figure 4A:
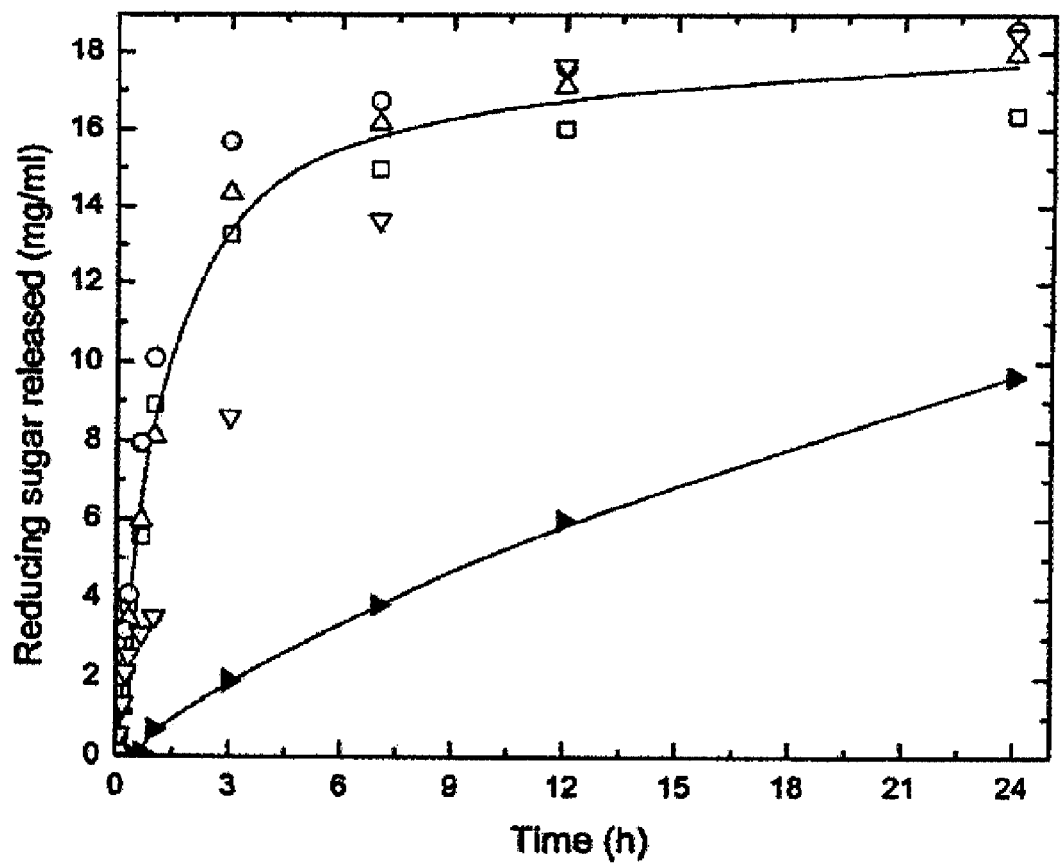
FIG. 4A: show hydrolysis rates of IL incubated samples compared to those of untreated Avicel (▸), 5% (□), 10% (○), 15% (Δ), 30% (∇). Avicel samples were incubated for 30 minutes in BMIMCl at 120° C. and precipitated with deionized water. Conversion of cellulose to sugars for batch samples of 17 mg/ml Avicel hydrolyzed with *T. reesei* cellulase activity of 16 FPU/g glucan and supplemental cellobiase activity of 83 CBU/g glucan at 50° C. is shown as a function of time for total soluble sugars (measured using a DNS assay).
Figure 4B:
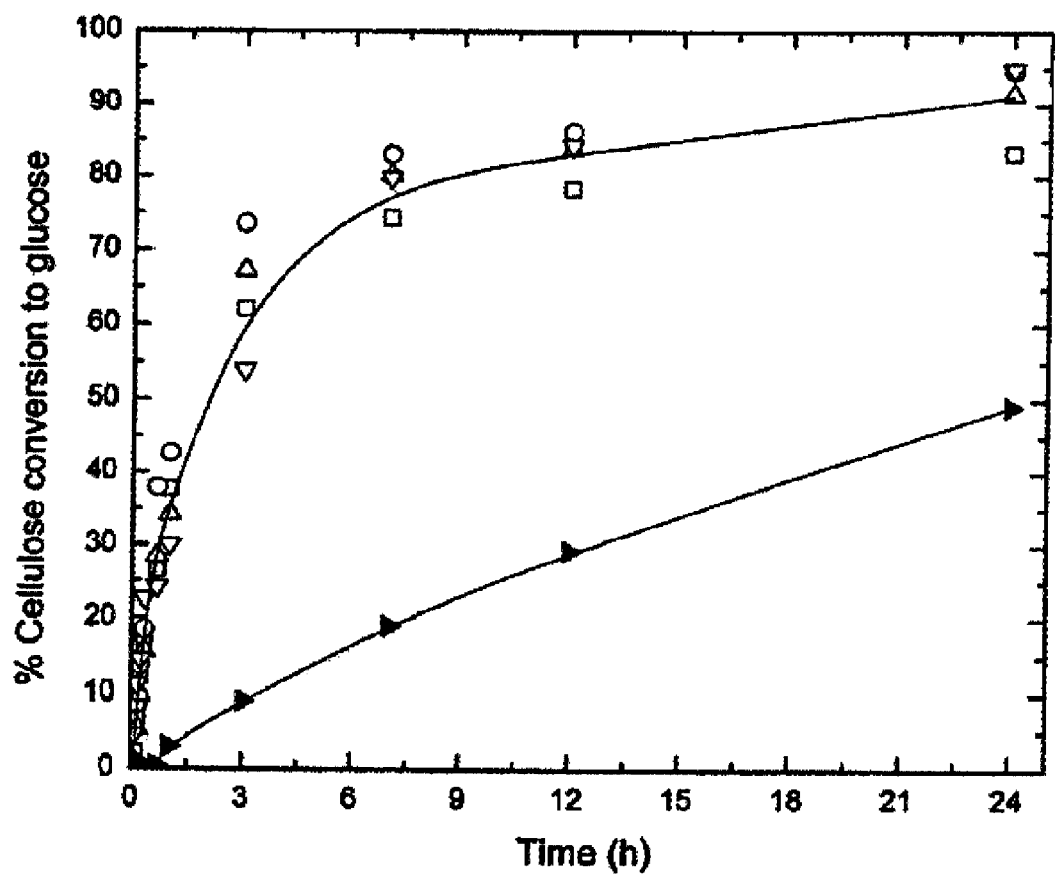
FIG. 4B: show hydrolysis rates of IL incubated samples compared to those of untreated Avicel (▸), 5% (□), 10% (○), 15% (Δ), 30% (∇). Avicel samples were incubated for 30 minutes in BMIMCl at 120° C. and precipitated with deionized water. Conversion of cellulose to sugars for batch samples of 17 mg/ml Avicel hydrolyzed with *T. reesei* cellulase activity of 16 FPU/g glucan and supplemental cellobiase activity of 83 CBU/g glucan at 50° C. is shown as % cellulose conversion to glucose (measured by HPLC).

For both RC (5% & 10%) and a mixture of RC and PCC (15% & 30%) samples, conversion to glucose after 7 hours of hydrolysis was about 80-85% whereas it is only 20% for untreated cellulose (FIGS. 3*b* and 4*b*). IL-treated-cellulose exhibited improved hydrolysis kinetics with optically transparent solutions formed after first few hours of reaction (within ~2 to 4 hours), indicating relatively fast hydrolysis kinetics and rapid conversion of cellulose into soluble oligimers of glucose and cellobiose. In contrast with untreated cellulose, solid cellulose is present even after extended hydrolysis times (greater than 24 hours). Cellulase and other enzymes are adsorbed on to solid cellulose substrate, resulting in difficult recovery and loss of these valuable enzymes. With the absence of residual solid cellulose in hydrolysates produced with IL-treated cellulose, enzymes are easily recovered.

Higher conversions were expected for RC samples as the crystallinity of cellulose is almost eliminated in RC samples. Higher conversions obtained for mixtures of RC and PCC (15% & 30%) are somewhat surprising. In spite of the residual crystallinity of these cases, the conversions were higher and comparable to that of RC samples (5% & 10%)

(FIGS. 3 & 4). This implies that the crystallinity of 15% and 30% cellulose samples treated in IL was reduced sufficiently to provide enough accessible sites for cellulase enzyme adsorption and activity. This is a promising observation as it suggests that it is not necessary to "totally eliminate" the crystallinity of cellulose to achieve significant enhancement in hydrolysis rates, and even with appreciable residual crystallinity most of the recalcitrance to hydrolysis can be mitigated. This also offers the possibility to process larger amounts of cellulose rapidly (i.e., up to 30 wt % of cellulose can be incubated in the IL-treatment step). All IL-treated cellulose samples reached almost 95% conversions to glucose within 24 h whereas untreated cellulose only reached 50% conversion in that time period (FIGS. 3 & 4).

The hydrolysis rates of IL-treated-cellulose samples within the solubility limit (5% & 10%) were comparable for cellulose incubated in either AMIMCl or BMIMCl. With IL-treated-cellulose samples above the solubility limit (15% & 30%), the hydrolysis rates appear to differ according to the dissolving capabilities of the ionic liquid. The hydrolysis rates of IL-treated-cellulose prepared from 15% and 30% Avicel incubation in BMIMCl were higher than those prepared with AMIMCl (Table 3).

SUMMARY & CONCLUSIONS

In a novel technique, the microcrystalline cellulose was incubated with an ionic liquid (IL) and then recovered as essentially amorphous or as a mixture of amorphous and partially crystalline cellulose, by rapidly quenching the IL-cellulose mixture with an anti-solvent. When the incubation samples contained initial cellulose weight percent above its solubility limit in the IL, subsequent anti-solvent treatment provides a cellulose mix of amorphous regenerated-cellulose (RC) and partially-crystalline-cellulose (PCC). The crystallinity index (CrI) obtained from XRD measurement of the IL-treated samples displayed a corresponding increase in CrI when the initial wt % of cellulose was above the solubility limit in the IL.

The IL-treated cellulose samples were hydrolyzed to sugars using commercial cellulases or cellulases supplemented with β-glucosidase. IL-treated-cellulose exhibited improved hydrolysis kinetics with optically transparent solutions formed after the first few hours of reaction, indicating relatively fast hydrolysis kinetics. With optimal IL-treatment conditions and enzyme loadings, initial rates of hydrolysis of IL-treated cellulose were two orders of magnitude higher than those observed with untreated-cellulose. Among IL-treated cellulose preparations, the initial rates observed with samples containing only RC were higher than the initial rates for the samples that were mixtures of RC and PCC. In spite of the observed differences in the initial rates and CrI, all IL-treated cellulose preparations showed significantly higher glucose conversions compared to untreated-cellulose: about 80-85% conversions to glucose were observed for IL-treated cellulose samples in 7 hours of hydrolysis whereas conversion for untreated-cellulose was only 20%. Thus, it is not necessary to completely eliminate the crystallinity of cellulose in order to achieve significant enhancement in hydrolysis rates; even with some residual crystallinity the recalcitrance to hydrolysis can be mitigated.

In the proposed technique, dissolution of cellulose in the IL and its subsequent precipitation with anti-solvent, allows separation of the IL/anti-solvent solution from cellulose by a simple filtration or centrifugation step. Due to the non-volatility of the IL, anti-solvent can be easily stripped from the IL/anti-solvent solution for recovery and recycle of both the ionic liquid and anti-solvent. These considerations point to the promise of the proposed technique in dealing with the recalcitrance of cellulose to hydrolysis.

MODIFICATIONS

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

We claim:

1. A method for the preparation of one or more alcohols comprising the steps of:
    incubating biomass cellulose or waste cellulose with an ionic liquid (IL) to form a solution;
    precipitating amorphous cellulose and/or cellulose of reduced crystallinity by admixture with an anti-solvent;
    adding cellulases to the cellulose precipitate under conditions which promote the hydrolysis of cellulose to sugars; and
    converting the sugars to one or more alcohols.

2. A method according to claim 1 wherein the solution admixture has a cellulose concentration below the solubility limit.

3. A method according to claim 1 wherein the solution admixture has a cellulose concentration above the solubility limit; and further comprises an undissolved swollen portion.

4. A method according to claim 1 further comprising the step of separating the cellulose precipitate from the anti-solvent prior to the addition of cellulases.

5. A method according to claim 1 wherein the ionic liquid is molten at a temperature ranging from −10° C. to 160° C. and comprises cations or anions.

6. A method according to claim 1 wherein the IL is any ionic liquid that dissolves cellulose represented by a cation structure that includes imidazolium, pyrroldinium, pyridinium, phosphonium, or ammonium.

7. A method according to claim 1 wherein the IL is represented by the structure:

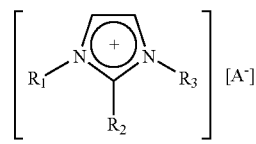

wherein each of R1, R2 and, R3 is hydrogen, an alkyl group having 1 to 10 carbon atoms or an alkene group having 2 to 10 carbon atoms, wherein the alkyl group may be substituted with sulfone, sulfoxide, thioether, ether, amide, or amine and wherein A is a halide, acetate, trifluoroacetate, dicyanamide, carboxylate or other anions.

8. A method according to claim 7 wherein the halide is a chloride, fluoride, bromide or iodide.

9. A method according to claim 1 wherein the IL is 1-n-butyl-3-methylimidazolium chloride.

10. A method according to claim 1 wherein the IL is 1-allyl-3-methyl imidazolium chloride.

11. A method according to claim 1 wherein the IL is 3-methyl-N-butylpyridinium chloride.

12. A method according to claim 1 wherein the anti-solvent is water, an alcohol or acetonitrile or any solvent which displaces the dissolved cellulose from the IL.

13. A method according to claim 12 wherein the alcohol is ethanol or methanol.

14. A method according to claim 1 wherein the IL is recovered from the anti-solvent through distillation, membrane separation, solid phase extraction, and liquid-liquid extraction.

15. A method according to claim 1 wherein the source of cellulose is waste cellulose.

16. A method according to claim 1 wherein the source of cellulose is biomass.

17. A method according to claim 1 wherein the cellulases include a mixture of enzymes.

18. A method according to claim 17 wherein the mixture of enzymes includes endo-gluconases, exo-glucanases, and β-glucosidases, and further wherein the enzyme mixture can be modified or simplified from conventional cellulase systems to achieve hydrolysis of IL-treated cellulose.

19. A method according to claim 1 wherein the cellulases are supplemented with β-glucosidase.

20. A method according to claim 1 wherein the improved hydrolysis rate allows saccharification with low enzyme loadings.

21. A method according to claim 1 wherein enzymes are recovered from cellulose hydrolysates.

22. A method according to claim 1 wherein the sugars are simple sugars or soluble oligomers.

23. A method according to claim 1 wherein the sugars are glucose.

24. A method according to claim 1 wherein the sugars are cellobiose.

25. A method according to claim 1 wherein the cellulose is native cellulose.

26. A method according to claim 25 wherein the native cellulose is crystalline or partially crystalline.

27. A method according to claim 1 wherein, the solution is subjected to either heating with agitation or microwave irradiation with intermittent agitation during incubation.

28. The method of claim 1, wherein the alcohol is ethanol.

* * * * *